United States Patent [19]

Avar et al.

[11] 3,975,382
[45] Aug. 17, 1976

[54] PYRAZOL(5)/PYRAZOLONE(5)METAL COMPLEXES AS STABILIZERS FOR ORGANIC MATERIALS

[75] Inventors: Lajos Avar, Binningen; Kurt Hofer, Munchenstein, both of Switzerland

[73] Assignee: Sandoz Ltd., Basel, Switzerland

[22] Filed: Mar. 14, 1975

[21] Appl. No.: 558,179

[30] Foreign Application Priority Data
Mar. 21, 1974 Switzerland.................... 3931/74

[52] U.S. Cl..................... 260/240 G; 260/45.75 N; 260/45.75 R; 260/45.75 C; 260/240.1; 260/240.3; 260/240.8; 260/299; 260/310 A; 260/310 R; 260/45.8 N
[51] Int. Cl.².................................. C07D 231/10
[58] Field of Search........... 260/240.1, 240.3, 240.8, 260/45.75 N, 45.75 R, 458 N, 429 J

[56] References Cited
UNITED STATES PATENTS
2,345,485  3/1944  Krzikalla et al................ 260/240 G
3,891,685  6/1975  Hari et al......................... 260/310

FOREIGN PATENTS OR APPLICATIONS
1,488,657  6/1967  France

OTHER PUBLICATIONS
Eldorfield, Heterocyclic Compounds, vol. 5, John Wiley & Sons, Inc., N.Y., N.Y., 1957, p. 111.
Dymek et al., Acta Pol. Pharm., vol. 20, (1963), pp. 9–14.
Passerini et al., Gazz. Chim. Ital., 69, pp. 658–664.
R101, Gazz. Chim Ital., vol. 77, 1948, pp. 3–12.

*Primary Examiner*—Arthur P. Demers
*Attorney, Agent, or Firm*—Gerald D. Sharkin; Richard E. Vila; Joseph J. Borovian

[57] ABSTRACT

The present invention concerns novel pyrazole (5) pyrazolone (5) metal complexes of the formula

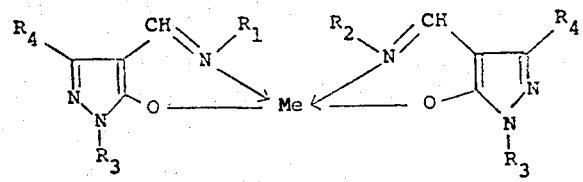

wherein $R_1$, $R_2$, $R_3$ and $R_4$ are substituents and Me is a transition metal, useful in stabilizing sensitive organic material against the degradative effect of U.V. light.

7 Claims, No Drawings

PYRAZOL(5)/PYRAZOLONE(5)METAL COMPLEXES AS STABILIZERS FOR ORGANIC MATERIALS

The present invention relates to pyrazole (5) pyrazolone (5) metal complexes useful in stabilising sensitive organic material against the degradative effect of U.V. light.

Accordingly the present invention provides compounds of formula I

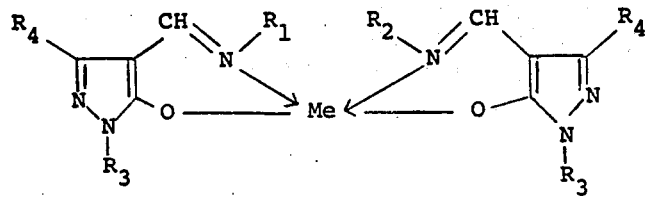

I wherein either

R$_1$ and R$_2$ are each, independently, one of the monovalent groups alkyl (C$_1$-C$_{22}$), monochloroalkyl (C$_1$-C$_{22}$), alkyl (C$_1$-C$_6$) substituted by a 5 or 6 membered heterocycle having 1 or 2 hetero atoms, phenylalkyl (C$_1$ or C$_2$), phenylalkyl (C$_1$ or C$_2$) substituted on the phenyl nucleus by 1 or 2 alkyl (C$_1$-C$_4$) groups and/or by hydroxy, phenyl or phenyl substituted by 1 to 3 alkyl (C$_1$-C$_{12}$) groups, 1 or 2 alkoxy (C$_1$-C$_8$) groups, ortho or para hydroxy, 1 to 3 halogen atoms, phenyl and/or phenoxy with 3 substituents and up to C$_{12}$ in the aggregate of the substituents, or a group of the formula II

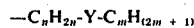 II wherein Y is -O-, -S-,

or

and each of $m$ and $n$ are, independently, an integer 1 to 5,
or R$_1$ and R$_2$ together form a 1,2-ethylene or 1,3-propylene bridge unsubstituted or substituted by 1 to 3 alkyl (C$_1$-C$_{22}$) groups with up to C$_{22}$ in the aggregate of the substituents,
R$_3$ and R$_4$ are each, independently, a substituent and in particular
each R$_3$ is, independently, alkyl (C$_1$-C$_8$), phenyl or phenyl substituted by 1 or 2 alkyl (C$_1$-C$_4$) groups or by 1 or 2 chlorine atoms
and each R$_4$ is, independently, alkyl (C$_1$-C$_4$) or phenyl,
and Me is Ni, Cu, Cd, Co, Mn or Zn.

The substituents R$_3$ and R$_4$ are selected so as not to unduly affect the stability or the U.V. stabilising properties of the compounds.

A preferred class of compounds are the compounds of formula I$a$

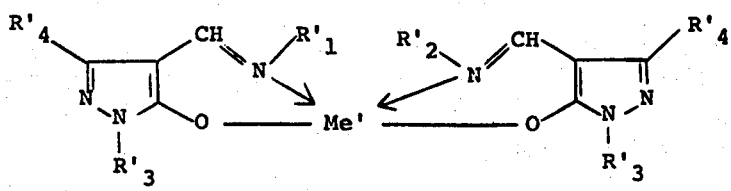

wherein each
R'$_1$ and R'$_2$ is, independently, one of the monovalent groups alkyl (C$_1$-C$_{18}$), alkyl (C$_1$-C$_6$) substituted by piperidino or morpholino, benzyl, benzyl substituted on the phenyl nucleus by 1 or 2 alkyl (C$_1$-C$_4$) groups and/or hydroxy, phenyl or phenyl substituted by 1 or 2 alkyls (C$_1$-C$_{12}$), 1 alkoxy (C$_1$-C$_4$), 1 ortho or para hydroxy and/or 1 chlorine with 1 to 3 substituents and up to C$_{12}$ in the aggregate thereof,
or R'$_1$ and R'$_2$ together form a 1,2-ethylene or 1,3-propylene bridge unsubstituted or substituted by 1 or 2 alkyl (C$_1$-C$_4$) groups,
each R'$_3$ is, independently, alkyl (C$_1$-C$_8$), phenyl or phenyl substituted by 1 or 2 alkyl (C$_1$-C$_4$) groups or 1 or 2 chlorine atoms,
each Me''$_4$ is, independently, alkyl (C$_1$-C$_4$) or phenyl, and Me' is Ni, Cu, Mn or Zn.

A further preferred class of compounds are the compounds of formula I$b$

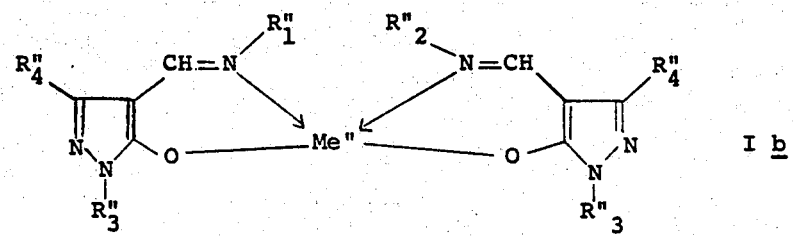

I$b$ wherein either $R_1''$ and $R_2''$ are each, independently, one of the monovalent groups alkyl ($C_1$-$C_{18}$), alkyl ($C_1$-$C_4$) substituted by piperidino or morpholino, benzyl, benzyl substituted on the phenyl nucleus thereof by an alkyl ($C_1$-$C_4$) substituent, phenyl or phenyl substituted by 1 or 2 ($C_1$-$C_{12}$) alkyl groups with $C_1$-$C_{12}$ in the aggregate of the substituents, or $R_1''$ and $R_2''$ together form a 1,2-ethylene or 1,3-propylene bridge, each $R_3''$, independently, is methyl, phenyl or phenyl substituted by an alkyl ($C_1$-$C_4$) group, each $R_4''$, independently, is alkyl ($C_1$-$C_3$) or phenyl, and me'' is Ni, Cu or Mn.

A still further preferred class of compounds are the compounds of formula Ic wherein $R_1'''$ and $R_2'''$ are each independently, alkyl ($C_1$-$C_{18}$), morpholino-ethyl or para-butyl phenyl, each $R_3'''$ is, independently, phenyl or phenyl substituted by methyl and each $R_4'''$ is, independently, alkyl ($C_1$-$C_3$).

Compounds of particular interest are the compounds of formula Id wherein $R_1'''$ and $R_2'''$ are as defined above.

By the term halogen as employed herein is meant chlorine or bromine.

When either of $R_1$ and $R_2$ is alkyl substituted by a heterocycle, then the heterocycle is preferably either aromatic or saturated and more preferably contains one hetero atom selected from oxygen, sulphur or nitrogen or one nitrogen and one oxygen as hetero atoms. In particular, the heterocycle is selected from 2-furanyl, 2-thienyl, piperidino and morpholino, especially the latter two.

When either of $R_1$ and $R_2$ are alkyl, this is preferably alkyl ($C_1$-$C_{18}$), more preferably alkyl ($C_4$-$C_{18}$).

When either of $R_1$ and $R_2$ are substituted alkyl, then the alkyl moiety is preferably $C_1$-$C_4$ alkyl, especially $C_1$-$C_3$, e.g. ethyl. The substituents are preferably piperidino or morpholino.

When either of $R_1$ and $R_2$ are substituted benzyl, the substituents are preferably selected from 1 or 2 ($C_1$-$C_4$) alkyls and/or hydroxy and more preferably the benzyl is monosubstituted by ($C_1$-$C_4$) alkyl.

When either of $R_1$ and $R_2$ are substituted phenyl, the substituents are preferably selected from 1 or 2 alkyls ($C_1$-$C_{12}$), alkoxy ($C_1$-$C_4$), ortho or para hydroxy and/or chlorine with 1 to 3 substituents and up to $C_{12}$ in the aggregate of the substituents, more preferably from 1 or 2 alkyls ($C_1$-$C_{12}$) with up to $C_{12}$ in the aggregate of the substituents and in particular the substituted phenyl is para-butyl phenyl, e.g. para-n or tert-butyl phenyl, especially the former.

When either of $R_1$ and $R_2$ form together a substituted bridge member then this is preferably substituted by 1 or 2 alkyls ($C_1$-$C_4$) and preferably the bridge member is 1,2-ethylene.

When $R_3$ is alkyl, this is preferably alkyl ($C_1$-$C_8$), more preferably alkyl ($C_1$-$C_6$), particularly alkyl ($C_1$-$C_3$), especially methyl.

When $R_3$ is substituted phenyl, this is preferably substituted by 1 or 2 alkyls ($C_1$-$C_4$) or 1 or 2 chlorine atoms, more preferably by 1 alkyl ($C_1$-$C_4$).

When $R_4$ is alkyl, this is preferably alkyl ($C_1$-$C_4$), more preferably ($C_1$-$C_3$), especially methyl.

Preferably $R_1$ and $R_2$ independently have one of the significances of $R_1'$ and $R_2'$ respectively, more preferably one of the significances of $R_1''$ and $R_2''$ respectively, especially $R_1'''$ and $R_2'''$ respectively.

Preferably $R_1$ and $R_2$ signify monovalent radicals.

Preferably $R_3$ has one of the significances of $R_3'$, more preferably of $R_3''$, especially $R_3'''$, and is particularly phenyl.

Preferably $R_4$ has one of the significances of $R_4'$, more preferably of $R_4'$, especially $R_4'''$, and is particularly methyl.

Preferably Me has one of the significances of Me', more preferably Me'' and in particular is Ni.

The term alkyl as employed herein is intended to cover straight or branched chain, primary, secondary or tertiary alkyls.

Examples of primary alkyl ($C_1$-$C_{22}$) groups that may be mentioned are the primary n- $C_4$, $C_5$, $C_6$, $C_8$, $C_9$, $C_{10}$, $C_{12}$, $C_{14}$, $C_{16}$ and $C_{18}$ alkyls.

Examples of secondary radicals are isopropyl, 2-butyl, 3-methyl-2-butyl, 2,2-dimethyl-3-octyl, 2-heptadecyl, 2-hexadecyl and 2-nonadecyl.

Examples of tertiary radicals are tertiary butyl, 3-methyl-3-hexyl and tert-octyl.

Examples of branched alkyl radicals are -2-methyl-1-propyl, 2,2-dimethyl-1-propyl and 2-methyl-1-butyl.

Examples of radicals of formula (II) are 2-methoxyethyl, 3-methoxypropyl, 2-methylthioethyl, methylthiomethyl, $C_2H_5COOC_3H_6-$, and $C_2H_5OOCC_3H_6-$.

Examples of substituted alkyl radicals are:

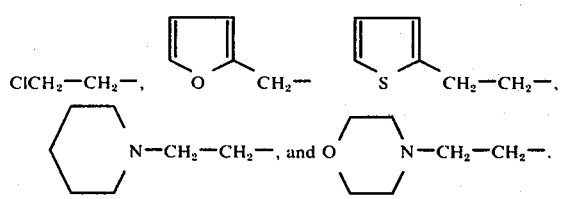

Examples of substituted phenyl- and phenyl alkyl radicals are:

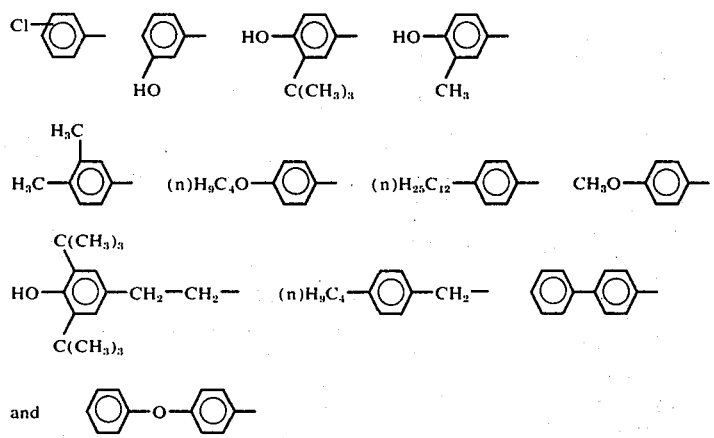

Preferably the compounds of formula I are symmetrical, that is to say either $R_1$ is the same as $R_2$ and the two sets of $R_3$ and $R_4$ are the same, or $R_3$ and $R_4$ are the same and $R_1$ and $R_2$ form a symmetrical bridge member.

The compounds of formula I are produced, in accordance with a further aspect of the present invention, by complexing one or more compounds of formula III

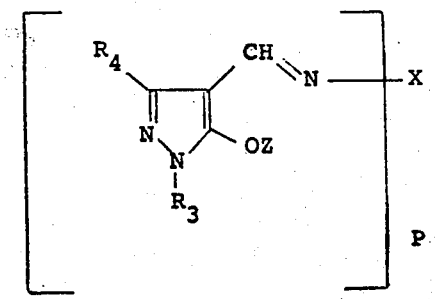

wherein
X has one of the significances of $R_1$ and/or $R_2$,
Z is hydrogen or an alkali metal ion, $R_3$ and $R_4$ are as defined above
and p is 1 or 2, with the provisos that when p is 1 then X is a monovalent group and when p is 2, X forms a divalent bridge member, with a complexable Me-salt.

The process may be effected for example in a solvent such as an alcohol, e.g. methanol, ethanol or n-propanol. The temperature may vary from room temperature to the reflux temperature of the solvent. Precipitation of the desired product may be initiated or accelerated by addition of water. Examples of suitable complexable Me salts are the chloride, acetate, sulphate, and tartrate salts, e.g. nickel chloride, nickel acetate, copper ammonium sulphate and sodium copper(I)-tartrate.

The alkali salt forms of the compounds of formula III may be produced from the hydroxy form by reaction with an alkali, e.g. NaOH or KOH, in manner known per se.

The compounds of formula IIIa

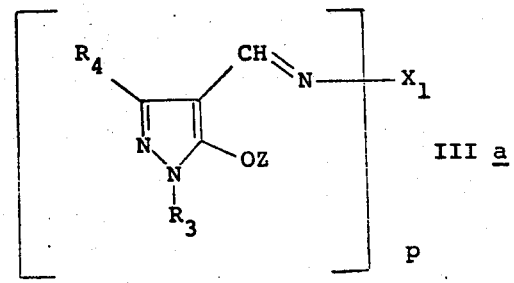

wherein
$R_3$, $R_4$, p and Z are as defined above
and $X_1$ has one of the significances of X defined above other than methyl, unsubstituted phenyl, or phenyl monosubstituted by alkoxy ($C_1$ or $C_2$),
are novel and also form part of the present invention.

The compounds of formula III may in general be produced in accordance with the known methods for producing Schiffs bases, e.g. by condensing a compound of formula IV

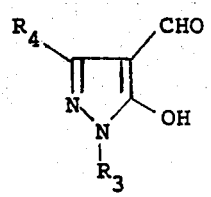

wherein $R_3$ and $R_4$ are as defined above with a compound of formula V $$X(NH_2)_p \qquad V$$

wherein X and p are as defined above and when Z of formula III is an alkali metal ion, converting the resulting compound to the corresponding salt.

The reaction may be effected in a solvent such as toluene, xylene or benzene at a temperature of 80°–150°C, more preferably 90°–120°C, especially at reflux temperature.

The compounds of formula I are useful in the stabilisation of sensitive organic material against the degradative effect of ultra-violet (U.V.) light.

Accordingly, the present invention provides a method of stabilising sensitive organic material against the degradative effect of U.V. light which comprises "treating" said material with an effective amount of a compound of formula I.

By the term "treating" as employed herein is meant surface coating or incorporating the compound on or in, respectively, the organic material. The compound is preferably incorporated in the body of the organic material and more preferably is uniformly distributed therein.

Sensitive organic materials to which the method of the invention is suited include natural and synthetic polymeric materials such as natural polyalkylenes, e.g. natural rubber, natural polyethers such as natural cellulose, e.g. cotton, and natural polyamides, e.g. wool and silk, and synthetic polymeric materials such as synthetic polyalkylenes especially polyethylene and polypropylene, polyesters especially polyethylene terephthalates, cellulose acetobutyrate, polyvinylchloride, polymethyl methacrylates, polyphenylene oxides, polystyrene, polyurethanes, polycarbonates, polyamides such as nylon and polypropylene oxide and including synthetic co- and terpolymers such as copolymers of styrene and acrylonitrile or of styrene and butadiene and terpolymers of acrylonitrile, butadiene and styrene (ABS) and acrylic esters, styrene and acrylonitrile.

Preferably, the material treated comprises synthetic polymeric material, particularly polyethylenes, polypropylenes, polyesters, polyamides, polyurethanes, polyacrylonitriles, copolymers of styrene and acrylonitrile or styrene and butadiene, acrylonitrile-butadiene-styrene terpolymers and terpolymers of acrylic esters, styrene and acrylonitrile.

The stabilised materials may be in solid forms, e.g. panels, rods, coatings, sheets, films, tapes, fibres, granules or powders or in liquid or paste forms, e.g. solutions or emulsions.

The material to be stabilised may be treated in conventional manner.

In the treatment of kneadable solid materials, one important embodiment of the method of the invention comprises intimately mixing the compounds with a particulate, e.g. granular, form of material, e.g. polypropylene in a kneader. The material may thereafter be formed into the required shape, e.g. by extrusion or injection moulding.

In the treatment of synthetic polymeric materials, a further important embodiment of the method of the invention comprises mixing the monomer or prepolymer with the compounds prior to polymerisation.

The amount of compound employed in the method of the invention will naturally vary depending for example on the compound employed, the material to be treated and the mode of treatment. However, in general, satisfactory results may be obtained when the amount of compound employed is in the range 0.01 to 5%, preferably 0.05 to 1% of the weight of the material to be treated.

In the following Examples the parts and percentages are by weight. The temperatures are in degrees centigrade. The structures of the obtained compounds are verified by microanalysis and spectral analysis.

EXAMPLE 1

6.06 g of 1-phenyl-3-methyl-4-formyl-pyrazolone(5) and 4 g of n-octylamine are refluxed in 80 cc of toluene for 1 hour. The solvent is then distilled off and the remaining yellow product having the formula

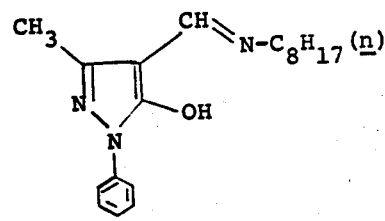

is dissolved in 50 cc of methanol. 3.72 g of nickel acetate tetrahydrate are added at 50°C to the methanolic solution which is then stirred over the course of 30 minutes and cooled to room temperature. The obtained green precipitate is suction filtered, washed with water and dried. The compound of formula

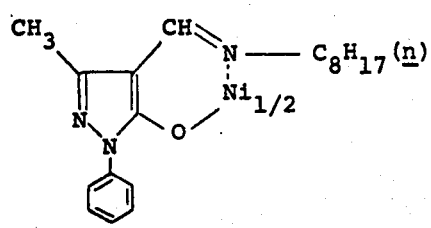

is obtained.

Elementary analysis: Calc.: C, 66.7%; H, 7.6%; N, 2.3%; Ni, 8.5%. Found: C, 66.3%; H, 7.3%; N, 12.5%; Ni, 9.1%.

EXAMPLE 2

6.06 g of 1-phenyl-3-methyl-4-formyl-pyrazolone(5) and 6.18 g of n-dodecylamine are refluxed in 80 cc of toluene in a flask, provided with water separator, until the theoretic amount of water is distilled off. The solvent is then removed with water-jet vacuum and the resulting dark oily product having the formula

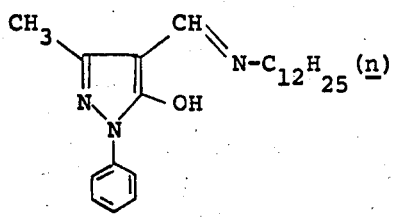

dissolved in 50 cc of methanol. 3.72 g of nickel acetate tetrahydrate are added at 40°C to this clear brown methanolic solution. A green precipitate is immediately obtained. After a period of 30 minutes the green precipitate is suction filtered, washed first with methanol and then with water and is dried. The compound of formula

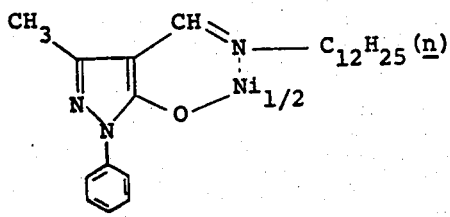

is obtained.

Elementary Analysis: Calc.: C, 69.5%; H, 8.6 %; N, 10.5%; Ni, 7.4%. Found: C, 69.8%; H, 8.5%; N, 10.4%; Ni, 7.5%.

EXAMPLE 3

10.1 g of 1-phenyl-3-methyl-4-formyl-pyrazolone(5) and 13.5 g of stearyl amine are refluxed in 200 cc of benzene for 1 hour. The benzene is distilled off and the resulting product having the formula

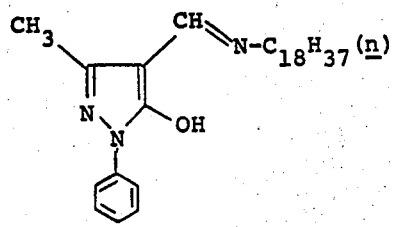

dissolved in 50 cc of methanol. 3.72 g of nickel acetate tetrahydrate are added at 40°C to this clear brown methanolic solution. A green precipitate is immediately obtained. After a period of 30 minutes the green precipitate is suction filtered, washed first with methanol and then with water and is dried. The compound of formula

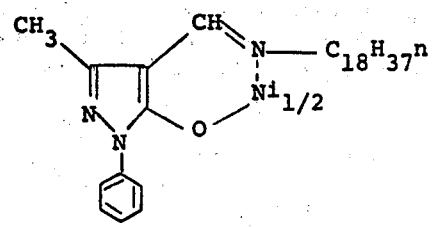

is obtained.

Elementary Analysis: Calc.: C, 72.4%; H, 9.5%; N, 8.7%; Ni, 6.0%. Found: C, 71.9%; H, 9.4%; N, 8.9%; Ni, 6.3%.

EXAMPLE 4

6.06 g of 1-phenyl-3-methyl-4-formyl-pyrazolone(5) and 6.16 g of dodecylamine are refluxed in 100 cc of toluene for 1 hour. The toluene is then distilled off and the resulting residue suspended in 40 cc of methanol. 3.7 g of cobalt acetate are added and the mixture is stirred for 30 minutes. The obtained precipitate is subsequently suction filtered, washed with water and dried. The compound of formula

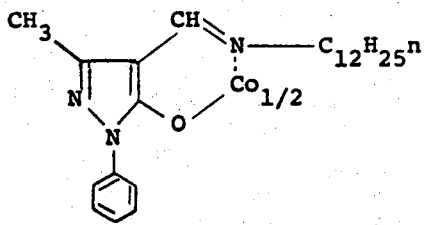

is obtained.

Elementary Analysis: Calc.: Co, 7.4%. Found: Co, 7.2%.

EXAMPLE 5

6.06 g of 1-phenyl-3-methyl-4-formyl-pyrazolone(5) and 6.16 g of dodecylamine are refluxed in 30 cc of toluene for 1 hour. The mixture is then cooled to 50°C, 80 cc of methanol and 3.0 g of copper acetate are added and stirring is effected for 30 minutes. The resulting green precipitate is suction filtered at room temperature, washed with water and dried. The compound of formula

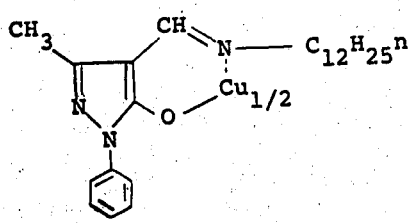

is obtained.

Elementary Analysis: Calc.: Cu, 7.9%. Found: Cu, 7.6%.

EXAMPLE 6

10.1 g of 1-phenyl-3-methyl-4-formyl-pyrazolone(5) and 5.3 g of benzylamine are refluxed in 75 cc of toluene for 2 hours. The solvent is then distilled off and the resulting brown product having the formula

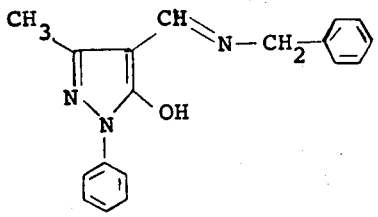

is dissolved in 50 cc of methanol. 6.2 g of nickel acetate-tetrahydrate are added at 50°C to the methanolic solution which is stirred for 30 minutes and cooled to room temperature. The obtained green precipitate is suction filtered, washed with water and dried. The compound of formula

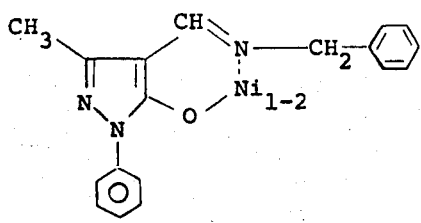

is obtained.

Elementary Analysis: Calc: Ni, 9.18%. Found: Ni, 8.9%.

EXAMPLE 7

8.5 g of the compound of the formula

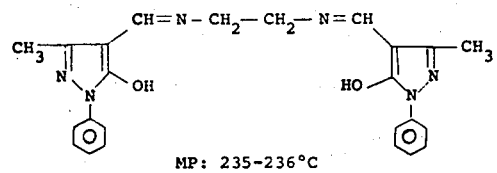

produced in analogous manner to the production of the intermediate described in Example 1 and employing ethylene diamine as starting material, are dissolved at 60°C in 100 g of methanol. 2.4 g of nickel acetate-tetrahydrate are added to this solution, the reaction product precipitating immediately. The mixture is stirred for 30 minutes, the obtained greenish precipitate is warm suction filtered, washed with methanol and dried. The compound of formula

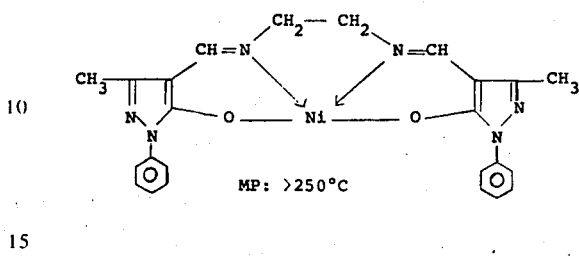

is obtained.

Elementary Analysis: Calc: Ni, 12.1%. Found: Ni, 12.2%.

The compounds of formula I and the corresponding starting materials of formula III (i.e. wherein Me is H) indicated in the table below are produced in analogous manner.

TABLE

| Nr. | $R_1$ | $R_4$ | $R_5$ | Me |
|---|---|---|---|---|
| 8 | $-CH_2-CH_2-N\diagdown O$ | ⌬- | $-CH_3$ | Ni |
| 9 | $-C_8H_{17}n$ | " | " | Co |
| 10 | " | " | " | Zn |
| 11 | " | " | " | Cu |
| 12 | $-C_8H_{17}n$ | $H_3C-$⌬- | $-CH_3$ | Ni |
| 13 | " | " | " | Co |
| 14 | " | " | " | Mn |
| 15 | $-C_{12}H_{25}$ | " | " | Ni |
| 16 | " | " | " | Mn |
| 17 | " | " | " | Cu |
| 18 | " | " | " | Zn |
| 19 | " | " | " | Co |
| 20 | $-C_{18}H_{37}$ | " | " | Ni |
| 21 | " | " | " | Cu |
| 22 | " | " | $-C_3H_7n$ | Ni |
| 23 | " | " | " | Co |
| 24 | " | " | " | Cu |
| 25 | " | " | " | Ni |
| 26 | $-C_{12}H_{25}$ | ⌬- | " | Ni |
| 27 | $-C_4H_9n$ | " | $-CH_3$ | Ni |
| 28 | $-C_5H_{11}n$ | " | " | Ni |
| 29 | $-C_6H_{13}n$ | " | " | Ni |
| 30 | " | " | " | Cu |
| 31 | $-C_6H_{13}$ | " | $-C_3H_7n$ | Ni |
| 32 | " | " | $-CH_3$ | Ni |
| 33 | ⌬-$C_4H_9(n)$ | " | " | Ni |
|  | ⌬-$C_{12}H_{25}$ |  |  |  |

Application Example

Unstabilised polypropylene and 0.5% of each of the compounds of Examples 1, 2, 3, 4, 8 and 26 are homogeneously kneaded on a roll mill at 180°C in manner known per se and the mixture is processed into sheets of 0.3 mm thickness. These sheets are tested for U.V. stability in the "Klimatest" apparatus by the De La Rue method at 40°C and 75% relative humidity, with thorough ventilation and irradiation by 16 sun lamps and 16 black lamps of Philips manufacture wherein U.V. stabilisation is indicated. Unstabilised polyvinyl chloride, containing 0.5% of the compound of Example 8 is tested in the "Klimatest" apparatus in analogous manner with similar result. Analogous results are obtained in polyethylene, acrylonitrile-butadiene-styrene (ABS) terpolymer, polyethylene terephthalate, cellulose acetobutyrate, polyamide 6, polystyrene, polycarbonate and polyurethane, incorporating each of the compounds of Examples 1, 2, 3, 4, 8 and 26.

What is claimed is:

1. A compound of the formula

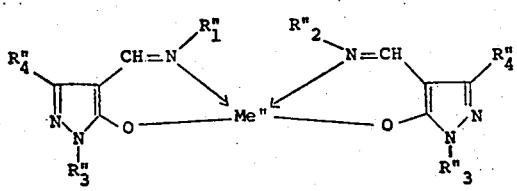

wherein either
$R_1''$ and $R_2''$ are each, independently, one of the monovalent groups alkyl ($C_1$-$C_{18}$), alkyl ($C_1$-$C_4$) substituted by piperidino or morpholino, benzyl, benzyl substituted on the phenyl nucleus thereof by an alkyl ($C_1$-$C_4$) substituent, phenyl or phenyl substituted by 1 or 2 ($C_1$-$C_{12}$) alkyl groups with $C_1$-$C_{12}$ in the aggregate of the substituents,
or $R_1''$ and $R_2''$ together form a 1,2-ethylene or 1,3-propylene bridge,
each $R_3''$, independently, is methyl, phenyl or phenyl substituted by an alkyl ($C_1$-$C_4$) group,
each $R_4''$, independently, is alkyl ($C_1$-$C_3$) or phenyl, and Me'' is Ni, Cu or Mn.

2. A compound of claim 1 of the formula

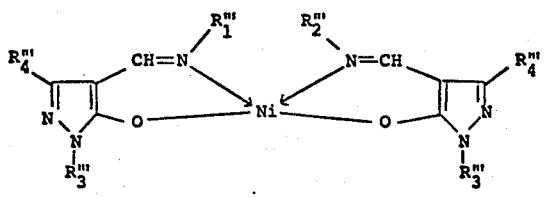

wherein
$R_1'''$ and $R_2'''$ are each, independently, alkyl ($C_1$-$C_{18}$), morpholino-ethyl or para-butyl phenyl,
each $R_3'''$ is, independently, phenyl or phenyl substituted by methyl,
and each $R_4'''$ is, independently, alkyl ($C_1$-$C_3$).

3. A compound of claim 2 of the formula

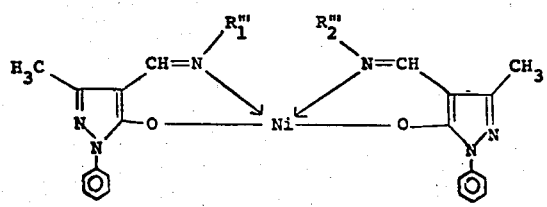

wherein $R_1'''$ and $R_2'''$ are as defined in claim 2.

4. A compound according to claim 3 wherein $R_1'''$ and $R_2'''$ are each a —$C_8H_{17}$ (n) group.

5. A compound according to claim 3 wherein $R_1'''$ and $R_2'''$ are each a —$C_{12}H_{25}$ (n) group.

6. A compound according to claim 3 wherein $R_1'''$ and $R_2'''$ are each a —$C_{18}H_{37}$ (n) group.

7. A compound according to claim 3 wherein $R_1'''$ and $R_2'''$ are each a

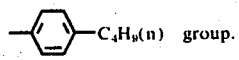

group.

* * * * *